United States Patent [19]

Thakur et al.

[11] Patent Number: 4,738,850

[45] Date of Patent: Apr. 19, 1988

[54] CONTROLLED RELEASE FORMULATION AND METHOD

[75] Inventors: Ajit B. Thakur, East Brunswick; Nemichand B. Jain, Monmouth Junction, both of N.J.

[73] Assignee: E. R. Squibb & Sons, Inc., Princeton, N.J.

[21] Appl. No.: 867,846

[22] Filed: May 27, 1986

[51] Int. Cl.$^4$ ............................ A61K 9/22; A61K 9/26
[52] U.S. Cl. .................................. 424/468; 424/469; 424/470
[58] Field of Search ................... 424/19, 22, 468, 469, 424/470

[56] References Cited

U.S. PATENT DOCUMENTS

| | | | |
|---|---|---|---|
| 3,458,622 | 7/1969 | Hill | 424/19 |
| 4,046,889 | 9/1977 | Ondetti et al. | 424/244 |
| 4,086,335 | 4/1978 | Bruscato et al. | 514/960 |
| 4,105,776 | 8/1978 | Ondetti et al. | 424/274 |
| 4,140,755 | 2/1979 | Sheth et al. | 424/21 |
| 4,168,267 | 9/1979 | Petrillo, Jr. | 260/326.2 |
| 4,221,778 | 9/1980 | Raghunathan | 424/31 |
| 4,337,201 | 6/1982 | Petrillo, Jr. | 548/413 |
| 4,432,971 | 2/1984 | Karanewsky et al. | 424/177 |
| 4,472,380 | 9/1984 | Harris et al. | 424/177 |
| 4,505,890 | 3/1985 | Jain et al. | 424/21 |

OTHER PUBLICATIONS

Sawayanagi et al., "Use of Chitosan for Sustained-Release Preparations of Water-Soluble Drugs", *Chem. Pharm. Bull.*, vol. 30, No. 11, (1982) pp. 4213–4215.

Kawashima et al., "Preparation of a Prolonged Release Tablet of Aspirin with Chitosan", *Chem. Pharm. Bull.*, vol. 33, No. 5, (1985) pp. 2107–2113.

Miyazaki et al., "Sustained Release of Indomethacin from Chitosan Granules", *Chem. Pharm. Bull.*, vol. 33, No. 9, (1985) pp. 3986–3992.

*Primary Examiner*—Shep K. Rose
*Attorney, Agent, or Firm*—L. S. Levinson; T. R. Furman, Jr.

[57] ABSTRACT

In accordance with the present invention, a controlled release formulation is provided from which a drug, selected from the group consisting of angiotensin converting enzyme inhibitors and ascorbic acid, is released at a substantially controlled rate. The controlled release formulation of the invention is comprised of a reactive matrix of from about 5 to about 80 percent by weight of the drug in combination with from about 5 to about 70 percent by weight of poly[(1→4)-2-amino-2-deoxy-$\beta$-D-glucose] (also referred to as chitosan herein). Further in accordance with the present invention there is provided a gel-like complex formed of the drug and the chitosan in environments ranging from neutral to acidic.

20 Claims, No Drawings

CONTROLLED RELEASE FORMULATION AND METHOD

FIELD OF THE INVENTION

The present invention relates to a controlled release formulation and more particularly concerns a formulation for the slow release of a drug which is part of a reactive matrix which includes chitosan polymer, that is, poly[(1→4)-2-amino-2-deoxy-$\beta$-D-glucose].

BACKGROUND OF THE INVENTION

Controlled release pharmaceutical formulations which provide for the uniform release of a medicament at a controlled rate over a desired extended period of time are of great benefit to both the patient and medical practitioner. Since the controlled release of many drugs is pH-dependent, certain dosage forms are not suitable for release in certain environments. For example, depending upon whether the controlled release is to be in the eyes, stomach, mouth, rumen, vagina, rectum, skin or gastrointestinal tract, the pH of the release environment can vary from neutral to acidic. For this reason, many controlled release systems that work in the human stomach do not work in the human intestinal tract and vice versa.

Numerous mechanisms have been employed for controlled release formulations. U.S. Pat. No. 3,458,622 to Hill discloses a controlled release tablet for the administration of medicinal agents over a prolonged period of up to about eight hours. This patent discloses a compressed tablet formed of a core containing a drug, a polymeric vinyl pyrrolidone, preferably polyvinyl pyrrolidone (PVP), and a carboxyvinyl hydrophilic polymer (hydrocolloid) such as those marketed under the trademark Carbopol, and a coating formed of the two polymeric substances on the core providing the controlled release effect by forming a complex under the action of water or gastric fluid. This complex is gel-like in consistency and retards the diffusion of the drug from the tablet.

U.S. Pat. No. 4,140,755 to Sheth et al. discloses a sustained release formulation in the form of sustained release tablets which are hydrodynamically balanced to have a bulk density (specific gravity) of less than one in contact with gastric fluid and which will therefore remain floating in gastric fluid which has a specific gravity of between 1.004 and 1.010. The Sheth et al. sustained release formulation contains a homogeneous mixture of one or more medicaments with one or more hydrophilic hydrocolloids, such as hydroxypropyl methyl cellulose having a viscosity of 4000 cps. The hydrocolloids when contracted with gastric fluid at body temperature form a sustained gelatinous mix on the surface of the tablet causing the tablet to enlarge and acquire a bulk density of less than one. The medicament is slowly released from the surface of the gelatinous mix which remains buoyant in the gastric fluid.

All of the medicament in the tablet disclosed in the Sheth et al. patent is released in the stomach.

Sawayanagi et al. (Chem. Pharm. Bull, 30(11):4213, 1982) have disclosed sustained release preparations for propanolol hydrochloride using poly[(1→4)-2-amino-2-deoxy-$\beta$-D-glucose] (chitosan). The chitosan forms a gel matrix for the controlled release of the drug. However, these preparations are pH-dependent in that the gel is only formed in an acidic environment and the tablets completely disintegrated in ten minutes at pH 6.8.

Kawashima et al. (Chem. Pharm. Bull. 33(5):2107, 1985) and Miyazaki et al. (Chem. Pharm. Bull. 33(9):3986, 1985) disclose tablet preparations for aspirin and indomethacin, respectively, using acetic acid which is a necessary addition to form the chitosan-drug mixtures for use in sustained release formulations.

U.S. Pat. No. 4,221,778 to Raghunathan et al. discloses a substantially pH-independent controlled release mechanism known as the Pennkinetic TM system which employs ion exchange resins. In this system, the drug is adsorbed onto the ion exchange resin particles and thereafter the particles are coated with a diffusion barrier. Ions from the environment diffuse through the coating and displace the drug molecules which subsequently diffuse out. However, loading of the drug molecules onto the resin particles is often inefficient. Further, preparations with water soluble drugs are typically unstable because the drugs are easily washed off of the resin particles (known to be hydrophobic) during processing.

Angiotensin converting enzyme (ACE) inhibitors are known for their usefulness as antihypertensive agents. Typical ACE inhibitors include substituted proline derivatives disclosed in U.S. Pat. No. 4,105,776 to Ondetti et al.; azetidine-2-carboxylic acid derivatives disclosed in U.S. Pat. No. 4,046,889 to Ondetti et al.; phosphinylalkanoyl prolines disclosed in U.S. Pat. No. 4,168,267 to Petrillo; phosphinylalkanoyl substituted prolines disclosed in U.S. Pat. No. 4,337,201 to Petrillo; phosphonamidate substituted amino or imino acids disclosed in U.S. Pat. No.4,432,971 to Karanewsky et al.; carboxyalkyl dipeptide derivatives disclosed in U.S. Pat. No. 4,472,380 to Harris et al.; and the like. Formulation of these and other drugs into controlled release systems is very difficult.

Accordingly, a controlled release formulation and method suitable for the sustained release of a medicament, such as angiotensin converting enzyme inhibitors, in a wide range of pH environments for administration to mammalian species would be a welcome addition to the art.

SUMMARY OF THE INVENTION

In accordance with the present invention, a controlled release formulation is provided from which a drug, selected from the group consisting of angiotensin converting enzyme inhibitors and ascorbic acid, is released at a substantially controlled rate. The controlled release formulation of the invention is comprised of a reactive matrix of from about 5 to about 80 percent by weight of the drug in combination with from about 5 to about 70 percent by weight of poly[(1→4)-2-amino-2-deoxy-$\beta$-D-glucose] (also referred to as chitosan herein). Further in accordance with the present invention there is provided a gel-like complex formed of the drug and the chitosan in environments ranging from neutral to acidic.

DETAILED DESCRIPTION OF THE INVENTION

The controlled release formulation of the present invention uses chitosan, that is, poly[(1→4)-2-amino-2-deoxy-$\beta$-D-glucose], a biodegradable, biocompatible polymer produced from the substantial (typically 80–90%) deacetylation of chitin, as the basis for its reactive matrix. The chitosan, in combination with a drug selected from the group consisting of angiotensin converting enzyme inhibitors and ascorbic acid, provides zero order release of the drug for a period of eight hours or more. Formulations comprising these drugs in combination with chitosan have not been heretofore disclosed.

The controlled release formulation of the invention may be in the form of sustained release solid dosage forms, such as tablets, capsules or suppositories and as such will further include one or more fillers or diluents, one or more lubricants and optionally one or more anti-adherents, water and/or any other conventional additives.

The chitosan and drug form a substantially homogeneous gel-like complex upon exposure to neutral or acidic liquids, e.g., water or acid, from which drug is slowly released over a desired period of time. Thus, the controlled release formulation of the present invention can be used in environments which are neutral, as well as acidic as distinguished from the prior art, and without the need for an added acidulent, e.g. acetic acid and the like.

The controlled release of the drug from the gel-like complex is pH-independent over the range from neutral to acidic. It is believed that the chitosan polymer acts as an ion exchange carrier for acidic drugs, e.g., ACE inhibitors and ascorbic acid, by virtue of its amino glucose moiety. Thus, the release mechanism is similar to that disclosed in the aforementioned U.S. Pat. No. 4,221,778 to Raghunathan et al. with the advantage that the present formulation forms its own gel on exposure to body (or similar) fluids and the drug is adsorbed throughout the gel. The present system obviates the need for ion exchange particles and additional gel coating as called for in the prior art. It is believed that drug release is provided by slow dissolution of the gel in either water or acid, diffusion of free drug through the gel, and the displacement of drug ions by ions from the stomach or gastrointestinal tract which have diffused through the gel complex. Thus, a uniform release of the drug in the gastrointestinal tract, or in other bodily environments which range from neutral to acidic, is possible.

The controlled release formulation of the invention may be formulated as a single mixture so that the gel-like complex will form, in situ, in the body or alternatively the gel-like complex can be formed prior to administration, and employed as such.

Angiotensin converting enzyme inhibitors suitable for use in the controlled release formulation of the present invention include substituted proline derivatives disclosed in U.S. Pat. No. 4,105,776 to Ondetti et al.; azetidine-2-carboxylic acid derivatives disclosed in U.S. Pat. No. 4,046,889 to Ondetti et al.; phosphinylalkanoyl prolines disclosed in U.S. Pat. No. 4,168,267 to Petrillo; phosphinylalkanoyl substituted prolines disclosed in U.S. Pat. No. 4,337,201 to Petrillo; phosphonamidate substituted amino or imino acids disclosed in U.S. Pat. No. 4,432,971 to Karanewsky et al.; carboxyalkyl dipeptide derivatives disclosed in U.S. Pat. No. 4,472,380 to Harris et al., and the like.

Preferred angiotensin converting enzyme inhibitors for use in the present formulation include 1-[(2S)-3-mercapto-2-methylpropionyl]-L-proline (captopril), that is

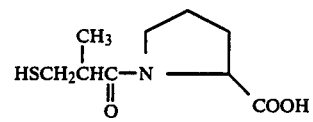

disclosed in U.S. Pat. No. 4,105,776 to Ondetti et al. and N-(1-ethoxycarbonyl-3-phenylpropyl)-L-alanyl-L-proline (enalapril), that is,

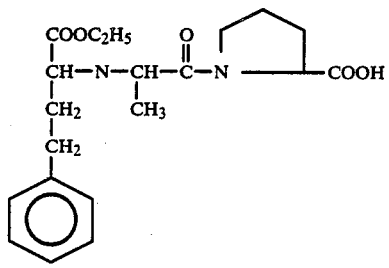

disclosed in U.S. Pat. No. 4,472,380 to Harris et al.

In forming the controlled release formulation of the present invention, the angiotensin converting enzyme inhibitor or ascorbic acid will be present in an amount within the range from about 5 to about 80 percent by weight of the formulation, and preferably from about 10 to about 70 percent by weight of the formulation, while the chitosan will be present in an amount within the range from about 5 to about 70 percent by weight and preferably from about 10 to about 60 percent by weight of the formulation.

For controlled release in accordance with the present invention, the ratio of drug, for example captopril, an angiotensin converting enzyme inhibitor, to chitosan will be from about 0.1:1 to about 15:1, preferably from about 0.3:1 to about 10:1, and optimally about 0.45:1 for controlled release over a period of eight hours or more.

When in the form of sustained release tablets, the controlled release formulation of the present invention will also include additional edible non-toxic ingredients as conventionally employed in solid medicinal dosage forms. Thus, the tablets of the invention will include from about 0 to about 30% by weight and preferably from about 1 to about 14% by weight of one or more diluents such as lactose, sugar, corn starch, citric acid, modified corn starch, mannitol, sorbitol, inorganic salts such as calcium phosphate or cellulose derivatives such as wood cellulose and microcrystalline cellulose, and one or more tableting lubricants in an amount within the range of from about 0.3 to about 8% by weight of the tablet, and preferably from about 0.3 to about 2% by weight of the tablet, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

A preferred sustained release tablet in accordance with the presen invention will include from about 10 to about 70 percent by weight of 1-(2S)-3-mercapto-2-methylpropionyl]-L-proline (captopril) or N-(1-ethoxycarbonyl-3-phenylpropyl)-L-alanyl-L-proline (enalapril), both ACE inhibitors, from about 10 to about 60 percent by weight of poly[(1→4)-2-amino-2-deoxy-β-D-glucose] (chitosan), from about 1 to about 14 percent by weight of a diluent, which is preferably lactose and from about 0.3 to about 2 percent by weight of a lubricant, which is preferably magnesium stearate.

The sustained release tablets of the invention may be prepared as follows. A mixture of the drug, chitosan, the diluent and lubricant is thoroughly mixed, for example, using a conventional blender. Thereafter, the so-formed mixture is compressed into tablets.

The controlled release formulation of the present invention is suitable for administration of angiotensin converting enzyme inhibitors or ascorbic acid to mammalian species, e.g., cows, cats, dogs, humans and the like.

EXAMPLE 1

A sustained release formulation in the form of a 211 mg tablet capable of slowly releasing the angiotensin converting enzyme inhibitor 1-[(2S)-3-mercapto-2-methylpropionyl]-L-proline (captopril) for a period of eight hours or more and having the following composition was prepared as described below.

| Ingredient | Amount (mg) | Weight Percent |
|---|---|---|
| 1-[(2S)—3-mercapto-2-methyl-propionyl]-L-proline (captopril) | 100.0 | 47.40 |
| poly[(1→4)-2-amino-2-deoxy-β-D-glucose] (chitosan) (90% deacetylation) | 100.0 | 47.40 |
| Lactose | 10.0 | 4.73 |
| Magnesium Stearate (lubricant) | 1.0 | 0.47 |

The 90% deacetylated chitosan was finely powdered in a hammer mill to obtain a 30-40 mesh powder. The chitosan powder was mixed with the captopril in a V-blender for 15 minutes. Thereafter, the lactose and magnesium stearate were added to the mixture. This mixture was then pressed into tablets.

The so-formed sustained release tablet of the invention was found to undergo substantially zero order release so that it slowly and uniformly releases drug over an 8 hour period in environments that range from neutral to acidic.

EXAMPLE 2

A sustained release formulation in the form of a 211 mg tablet capable of slowly releasing ascorbic acid for a period of eight hours or more and having the following composition was prepared as described below.

| Ingredient | Amount (mg) | Weight Percent |
|---|---|---|
| Ascorbic acid | 100.0 | 47.40 |
| poly[(1→4)-2-amino-2-deoxy-β-D-glucose] (chitosan) (90% deacetylation) | 100.0 | 47.40 |
| Lactose | 10.0 | 4.73 |
| Stearic acid (lubricant) | 1.0 | 0.47 |

The 90% deacetylated chitosan was finely powdered in a hammer mill to obtain a 30-40 mesh powder. The chitosan powder was mixed with the ascorbic acid in a V-blender for 15 minutes. Thereafter, the lactose and stearic acid were added to the mixture. This mixture was then pressed into tablets.

The so-formed sustained release tablet of the invention was found to undergo substantially zero order release so that it slowly and uniformly releases drug over an 8 hour period in environments that range from neutral to acidic.

What is claimed is:

1. A controlled release formulation from which a drug selected from the group consisting of angiotensin converting enzyme inhibitors and ascorbic acid is released at a substantially controlled rate in environments which are neutral or acidic consisting of a reactive matrix of from about 5 to about 80 percent by weight of said drug in combination with from about 5 to about 70 percent by weight of poly[(1→4)-2-amino-2-deoxy-β-glucose].

2. The formulation of claim 1 comprising from about 10 to about 70 percent by weight of said drug and from about 10 to about 60 percent by weight of said glucose.

3. The formulation of claim 1 wherein said drug and said glucose are in a weight ratio from about 0.1:1 to about 15:1.

4. The formulation of claim 3 wherein said drug and said glucose are in a weight ratio from about 0.3:1 to about 10:1.

5. The formulation of claim 3 wherein said drug and said glucose are in a weight ratio of about 0.45:1.

6. The formulation of claim 1 wherein said angiotensin converting enzyme inhibitor is selected from the group consisting of substituted proline derivatives, azetidine-2-carboxylic acid derivatives, phosphinylalkanoyl prolines, phosphinylalkanoyl substituted prolines, phosphonamidate substituted amino or imino acids, and carboxyalkyl dipeptide derivatives.

7. The formulation of claim 6 wherein said substituted proline derivative is 1-[(2S)-3-mercapto-2-methylpropionyl]-L-proline.

8. The formulation of claim 6 wherein said carboxyalkyl dipeptide derivative is N-(1-ethoxycarbonyl-3-phenylpropyl)-L-alanyl-L-proline.

9. A sustained release tablet formulation consisting of from about 5 to about 80 percent by weight of a drug, selected from angiotensin converting enzyme inhibitors and ascorbic acid, in combination with from about 5 to about 70 percent by weight of poly [(1→4)-2-amino-2-deoxy-β-glucose], from about 0 to about 30 percent by weight of a diluent and from about 0.3 to about 8 percent by weight of a lubricant.

10. The formulation of claim 9 wherein said diluent is selected from the group consisting of lactose, sugar, corn starch, modified corn starch, citric acid, mannitol, sorbitol, inorganic salts, or cellulose.

11. The formulation of claim 10 wherein said diluent is lactose.

12. The formulation of claim 9 wherein said lubricant is selected from the group consisting of magnesium stearate, stearic acid, palnitic acid, calcium stearate, talc, or carnauba wax.

13. The formulation of claim 12 wherein said lubricant is magnesium stearate.

14. The formulation of claim 1 in the form of a gel-like complex.

15. A method for the controlled release of a drug selected from the group consisting of angiotensin converting enzyme inhibitors and ascorbic acid in a neutral or acidic environment within a mammalian specie comprising (a) exposing the formulation of claim 1 or 9 containing an effective amount of said drug to a neutral or acidic liquid, thereby forming a gel-like complex; and thereafter, (b) subjecting said complex to said neutral or acidic environment such that the drug is slowly and substantially uniformly released over a period of 8 hours or more.

16. The method of claim 15 wherein step (a) is carried out prior to administration of said formulation to said specie.

17. The method of claim 15 wherein step (a) is carried out after administration of said formulation to said specie.

18. A method of alleviating hypertension in a mammalian specie which comprises administering the controlled release formulation of claim 6 containing an effective amount of said angiotensin converting enzyme inhibitor.

19. The method of claim 18 wherein said angiotensin converting enzyme inhibitor is 1-[(2S)-3-mercapto-2-methylpropionyl]-L-proline.

20. The method of claim 18 wherein said angiotensin converting enzyme inhibitor is N-(1-ethoxycarbonyl-3-phenylpropyl)-L-alanyl-L-proline.

* * * * *